United States Patent
Terashi

(10) Patent No.: US 9,765,024 B2
(45) Date of Patent: Sep. 19, 2017

(54) SYSTEM AND METHOD FOR ORGANIC SOLVENT PURIFICATION

(71) Applicant: ORGANO CORPORATION, Tokyo (JP)

(72) Inventor: Ryosuke Terashi, Tokyo (JP)

(73) Assignee: ORGANO CORPORATION, Tokyo (JP)

( * ) Notice: Subject to any disclaimer, the term of this patent is extended or adjusted under 35 U.S.C. 154(b) by 0 days.

(21) Appl. No.: 15/327,504

(22) PCT Filed: Jul. 22, 2015

(86) PCT No.: PCT/JP2015/070784
§ 371 (c)(1),
(2) Date: Jan. 19, 2017

(87) PCT Pub. No.: WO2016/017491
PCT Pub. Date: Feb. 4, 2016

(65) Prior Publication Data
US 2017/0158635 A1  Jun. 8, 2017

(30) Foreign Application Priority Data

Jul. 29, 2014 (JP) ................................ 2014-153572

(51) Int. Cl.
| | |
|---|---|
| *B01D 3/10* | (2006.01) |
| *B01D 61/58* | (2006.01) |
| *C02F 1/20* | (2006.01) |
| *C07D 207/267* | (2006.01) |
| *B01D 61/36* | (2006.01) |
| *B01D 15/36* | (2006.01) |
| *B01D 19/00* | (2006.01) |
| *C02F 1/44* | (2006.01) |
| *C02F 1/42* | (2006.01) |
| *C02F 103/34* | (2006.01) |

(52) U.S. Cl.
CPC ........... *C07D 207/267* (2013.01); *B01D 3/10* (2013.01); *B01D 15/363* (2013.01); *B01D 19/0031* (2013.01); *B01D 61/362* (2013.01); *B01D 61/58* (2013.01); *C02F 1/20* (2013.01); *C02F 1/448* (2013.01); *B01D 2311/02* (2013.01); *B01D 2311/06* (2013.01); *C02F 2001/422* (2013.01); *C02F 2103/34* (2013.01)

(58) Field of Classification Search
None
See application file for complete search history.

(56) References Cited

U.S. PATENT DOCUMENTS

| | | |
|---|---|---|
| 5,523,419 A | 6/1996 | Arnold |
| 5,556,539 A | 9/1996 | Mita et al. |

FOREIGN PATENT DOCUMENTS

| | | |
|---|---|---|
| JP | 63-258601 | 10/1988 |
| JP | 2-95419 | 4/1990 |
| JP | 6-199830 | 7/1994 |
| JP | 6-262042 | 9/1994 |
| JP | 6-277456 | 10/1994 |
| JP | 07-80252 | 3/1995 |
| JP | 07-194942 | 8/1995 |
| JP | 8-109167 | 4/1996 |
| JP | 11-276801 | 10/1999 |
| JP | 2004-105797 | 4/2004 |
| JP | 2013-18747 | 1/2013 |
| KR | 10-2013-0060471 | 6/2013 |
| KR | 10-1487107 | 1/2015 |
| WO | 2012/157525 | 11/2012 |

OTHER PUBLICATIONS

International Search Report issued in Patent Application No. PCT/JP2015/070784, dated Sep. 1, 2015.
Korean Office Action issued in Counterpart Patent Appl. No. 10-2016-7021174 dated Jul. 4, 2017, along with an English translation thereof.

*Primary Examiner* — Kristin Vajda
(74) *Attorney, Agent, or Firm* — Greenblum & Bernstein, P.L.C.

(57) ABSTRACT

An organic solvent purification system that separates an organic solvent having a boiling point of more than 100° C. at 1 atm, such as N-methyl-2-pyrrolidone (NMP), from a liquid mixture containing the organic solvent and water and purifies the organic solvent includes: a heater that heats the liquid mixture; a pervaporation apparatus that includes a pervaporation membrane, and is provided at subsequent position of the heater, the pervaporation apparatus separating the organic solvent from the water; a vacuum evaporator to which the organic solvent collected from a concentration side of the pervaporation apparatus is supplied; and piping that supplies the heater with the organic solvent vaporized in the vacuum evaporator as a heat source of the heater. The heater heats the liquid mixture using concentration heat of the organic solvent vaporized by the vacuum evaporator.

18 Claims, 3 Drawing Sheets

SYSTEM AND METHOD FOR ORGANIC SOLVENT PURIFICATION

TECHNICAL FIELD

The present invention relates to a system and method of separating an organic solvent represented by N-methyl-2-pyrrolidone (hereinafter, also referred to as NMP) from a liquid mixture containing the organic solvent and water and purifying the organic solvent, and more particularly to a system and method of organic solvent purification using pervaporation.

BACKGROUND ART

Some organic solvents have high solubility in water. When such water-soluble organic solvents are collected after being used so as to be reused, liquid mixtures containing the organic solvents and water are often collected, so that it is required to separate the organic solvents targeted for reuse from the liquid mixtures and then purify the organic solvents. The collected liquid mixtures are likely to contain impurities, such as ionic materials and fine particles, other than the organic solvents and water. Depending on the usage manner or the collecting manner of the organic solvents, the liquid mixtures might contain dissolved gases, such as dissolved oxygen and dissolved carbon dioxide.

NMP that is one of organic solvents having high solubility in water is widely used, for example, as a dispersion medium for slurry in which particles such as electrode active materials are dispersed when the slurry is applied onto electrode collectors and dried to form electrodes in a manufacturing process of lithium ion secondary batteries. NMP is collected while the slurry is dried, and the collected NMP can be reused after being purified. In the collection of NMP, vaporized NMP is collected by a water scrubber, for example. Hence, NMP is collected as a liquid mixture in which NMP and water are mixed. At this time, NMP concentration in this collected liquid mixture is approximately 70 to 90 mass %. Since the water scrubber is used, oxygen and carbon dioxide derived from the atmosphere are dissolved in the liquid mixture.

As a conventional method of separating and recovering an organic solvent from a liquid mixture containing the organic solvent and water, a distillation method has been known. More particularly, a vacuum distillation method of reducing pressure of the liquid mixture to distil this liquid mixture has been often used. However, there are some problems in the distillation method and the vacuum distillation method that these methods require a large amount of energy, and require a large-scale distillation facility in order to purify the organic solvent to a desired purity level. To cope with this, there has been known a pervaporation (PV) method as a separation method requiring no large-scale facility and excellent in energy saving performance.

In the pervaporation method, a separation membrane having high affinity with a component targeted for separation processing, such as water, is used. A liquid mixture containing this target component, such as a liquid mixture containing an organic solvent and water is brought to flow toward a supply side of the separation membrane, and pressure is reduced or an inert gas is brought to flow on a permeation side of the separation membrane, thereby carrying out separation utilizing differences in permeation rate among respective components through the separation membrane. A separation membrane used in the pervaporation method is also referred to as a pervaporation membrane. As a separation membrane through which water is brought to pass, a zeolite membrane is used, for example. If only water component moves toward the permeation side through the separation membrane, the organic solvent remains on the supply side of the separation membrane, thereby recovering the organic solvent. If separation between water and the organic solvent is carried out with the pervaporation method, heating is required for efficient separation. As a removal method of ionic impurities contained in organic solvents, there has been known a method using an ion exchange resin, for example.

Patent Literature 1 discloses, as an NMP separation system to separate NMP from a liquid mixture of NMP and water, a system in which a pervaporation apparatus is used and an ion exchanger is provided subsequent to the pervaporation apparatus.

FIG. 1 illustrates an example of a configuration of an organic solvent purification system in background art, equipped with a pervaporation apparatus and an ion exchanger disposed subsequent to this pervaporation apparatus. Herein, the system shown in FIG. 1 will be described, assuming that the organic solvent is NMP, for example. A liquid mixture containing NMP and water at ordinary temperature is heated up to approximately 120° C. by heater 12, and is then supplied to pervaporation apparatus 13. Steam is used as a heat source of heater 12. Inside pervaporation apparatus 13, there is provided pervaporation membrane 14 made of zeolite, for example. Water in the liquid mixture passes through pervaporation membrane 14, and thereafter, is cooled to be condensed by condenser 16, and is then discharged. Meanwhile, NMP does not pass through pervaporation membrane 14, and thus NMP is directly discharged in its liquid state from a concentration side of pervaporation apparatus 13. NMP discharged from pervaporation apparatus 13 is cooled by cooler 15. NMP at ordinary temperature obtained in this manner is then supplied to ion exchanger 17 so as to remove ionic impurities therefrom. Furthermore, fine particles are removed from this NMP by microfiltration (MF) membrane 18, and then NMP is stored as purified NMP in a tank or the like, or is sent to a process where this NMP is used.

In the organic solvent purification system shown in FIG. 1, there is a problem that, if an ion exchange resin inside ion exchanger 17 is broken, impurities such as sodium and silicon derived from a separation membrane and a filtration membrane located in the system might remain in the purified organic solvent such as NMP. Ion exchanger 17 is provided subsequent to pervaporation apparatus 13. Since ion exchanger 17 is required to remove ions from NMP that is a non-aqueous solvent, there is a problem that an ion exchange efficiency is small and thus a great labor is also required for replacement of the ion exchange resin.

After the organic solvent is separated from water by the pervaporation apparatus, as a method of further purifying this organic solvent, there has been known a method in which an evaporator is provided subsequent to the pervaporation apparatus so as to distil the organic solvent by this evaporator. This method is used for alcohol purification or the like. FIG. 2 illustrates an example of a configuration of an organic solvent purification system of background art in which the pervaporation apparatus and the evaporator are combined. In this system, ion exchanger 17 and microfiltration membrane 18 are omitted from the system shown in FIG. 1, and evaporator 20 heated by steam is provided between a concentration side of pervaporation apparatus 13 and cooler 15, instead. The organic solvent obtained from the concentration side of pervaporation apparatus 13 is distilled and purified in evaporator 20, and is condensed and cooled in cooler 15. Thereafter, the purified organic solvent is reserved in a tank or the like, or is sent to a process where the organic solvent is used. The ionic impurities, the fine particles and the like having been contained in the organic solvent are left in evaporator 20.

CITATION LIST

Patent Literature(s)

Patent Literature 1: JP 2013-18747A

SUMMARY OF INVENTION

Technical Problem

The pervaporation method as a method of separating organic solvents such as NMP from water is more excellent in energy saving performance, compared with a distillation method. However, if the evaporator is provided subsequent to the pervaporation apparatus for the purpose of removal of ionic impurities, fine particles and the like, additional energy is required to be supplied for the distillation. Consequently, there is caused a problem that it becomes difficult to sufficiently exert an advantage of energy saving attained by using the pervaporation apparatus. In addition, in the pervaporation method itself, a liquid to be supplied to the pervaporation apparatus is required to be heated, and thus there is room for improvement of further energy saving.

An object of the present invention is to provide an organic solvent purification system and an organic solvent purification method using a pervaporation method and capable of securely removing ionic impurities, fine particles and the like as well as attaining an energy saving performance.

Solution to Problem

An organic solvent purification system according to the present invention is a system that separates an organic solvent having a boiling point of more than 100° C. at 1 atm from a liquid mixture containing water and the organic solvent, and purifies the organic solvent, the system including: a heater that heats the liquid mixture; a pervaporation apparatus that includes a pervaporation membrane, and is provided at subsequent position of the heater, the pervaporation apparatus separating the organic solvent from the water; a vacuum evaporator to which the organic solvent collected from a concentration side of the pervaporation apparatus is supplied; and piping that supplies the heater with the organic solvent vaporized in the vacuum evaporator as a heat source of the heater.

An organic solvent purification method according to the present invention is a method that separates an organic solvent having a boiling point of more than 100° C. at 1 atm from a liquid mixture containing water and the organic solvent, and purifies the organic solvent, the method including the steps of: heating the liquid mixture; separating the heated liquid mixture into the organic solvent and the water using a pervaporation membrane; and carrying out vacuum evaporation of the organic solvent collected from a concentration side of the pervaporation membrane, wherein the organic solvent vaporized through the vacuum evaporation is used as a heat source in the heating step.

In the present invention, condensation heat of the organic solvent vaporized in the vacuum evaporator is recovered to be used as a heat source of the pervaporation apparatus. Hence, part or entire amount of heat supplied to the vacuum evaporator is recycled in the system, thereby reducing amount of energy required in the entire system. Amount of heat required in the pervaporation is mainly evaporative latent heat of the contained water component. Since the evaporative latent heat per unit mass of water is generally greater than that of an organic solvent, a heat recovery efficiency is high even if the amount of water in the liquid mixture supplied to the pervaporation apparatus is small. Meanwhile, since the vacuum evaporator is additionally provided, ionic impurities and fine particles in the organic solvent are left in the vacuum evaporator. Therefore, according to the present invention, it is possible to securely remove ionic impurities and fine particles while attaining energy saving performance.

DESCRIPTION OF EMBODIMENTS

Figure 1:
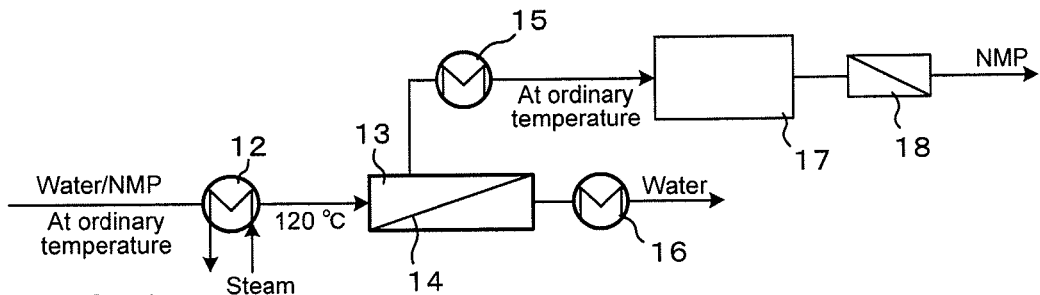
FIG. 1 is a view illustrating an example of a configuration of an organic solvent purification system of background art.
Figure 2:
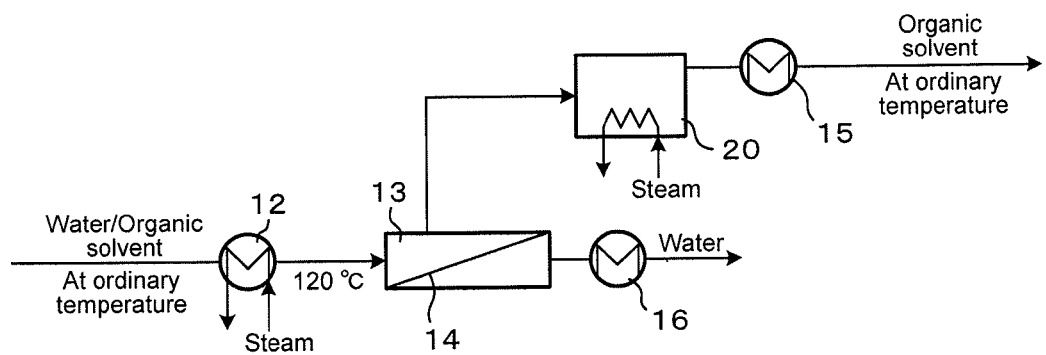
FIG. 2 is a view illustrating another example of the configuration of the organic solvent purification system of background art.
Figure 3:
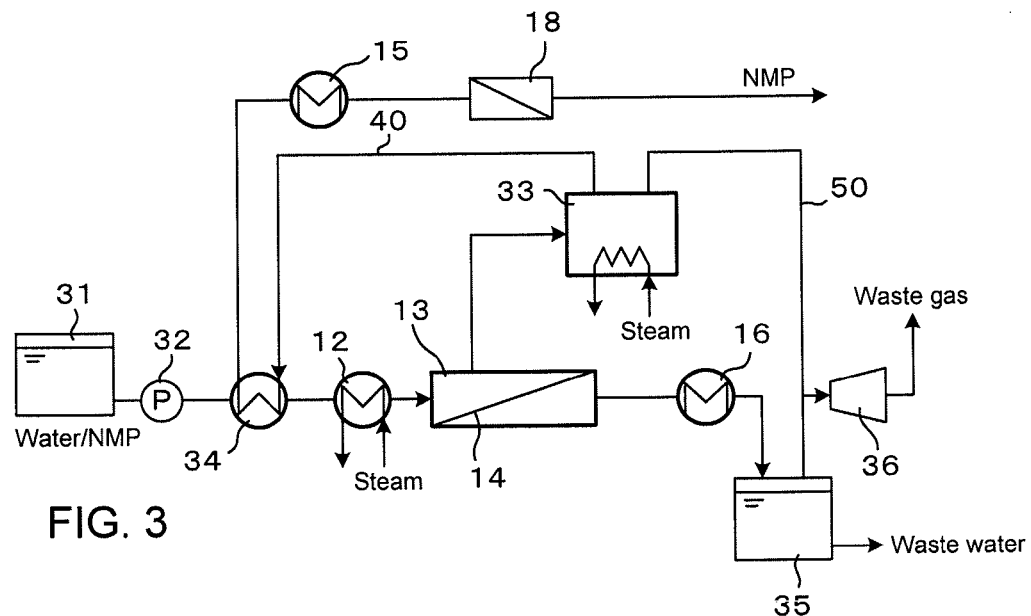
FIG. 3 is a view illustrating a configuration of an organic solvent purification system according to one embodiment of the present invention.

Preferred embodiments of the present invention will be described with reference to drawings, hereinafter. FIG. 3 illustrates a basic mode of an organic solvent purification system based on the present invention as an organic solvent purification system according to one embodiment of the present invention. The organic solvent purification system is configured to separate an organic solvent from a liquid mixture containing the organic solvent and water and then purify the organic solvent. The system is used, for example, for processing a liquid mixture containing water and NMP (N-methyl-2-pyrrolidone) collected in a manufacturing process of lithium ion secondary batteries, and separating NMP from this liquid mixture to purify NMP. Hereinafter, the case of using NMP as an organic solvent will be described, but the organic solvent to which the present invention is applicable is not limited to NMP. The present invention is also applicable to an organic solvent generally having a boiling point at an atmospheric pressure (0.1013 MPa) higher than a boiling point of water (100° C.), preferably having a boiling point under the atmospheric pressure of not less than 120° C., which is a usual operation temperature of the pervaporation apparatus. An example of such an organic solvent is shown in Table 1. In Table 1, the boiling point is indicated in a value at 0.1013 MPa. In addition, as an organic solvent to which the present invention is applicable, it is more preferable to use an organic solvent that produces no azeotropic mixture with water. For example, among organic solvents shown in Table 1, those except for PGME, PEGMEA and pyridine are organic solvents producing no azeotropic mixture with water.

TABLE 1

| Name | Boiling point (° C.) |
|---|---|
| N-methyl-2-pyrrolidone (NMP) | 202 |
| 1-methoxy-2-propanol (PGME) | 120 |
| Propylene glycol-1-monomethyl ether-2-acetate (PEGMEA) | 146 |
| Pyridine | 115 |
| Dimethyl sulfoxide (DMSO) | 189 |
| Monoethanolamine (MEA) | 170 |
| N,N-dimethylformamide (DMF) | 153 |
| γ-butyrolactone (GBL) | 204 |
| Dimethylacetamide (DMA) | 165 |

There is provided raw solution tank 31 in which the liquid mixture containing NMP and water is reserved, and the liquid mixture in raw solution tank 31 is supplied to pervaporation apparatus 13 by pump 32. Between pump 32 and pervaporation apparatus 13, heater 34 and heater 12 for heating the liquid mixture are provided in this order. Subsequent heater 12 is supplied with steam, and the liquid mixture is heated by the steam. The liquid mixture supplied to pervaporation apparatus 13 is heated up to approximately 120° C., for example.

Pervaporation apparatus 13 is provided with pervaporation membrane 14 formed by zeolite, for example, and the liquid mixture is separated into NMP and water through this membrane. Water passes through pervaporation membrane 14, so that water flows out in the form of water vapor from an outlet on the permeation side of pervaporation apparatus 13. This water vapor is cooled and condensed by condenser 16, and is reserved in permeation water tank 35, and is then discharged therefrom. Meanwhile, NMP does not pass through pervaporation membrane 14, so that NMP is discharged from an outlet provided on a concentration side in pervaporation apparatus 13, and is then supplied to vacuum evaporator 33. Vacuum evaporator 33 is connected via piping 50 that is a vacuum line to vacuum pump 36 that reduces pressure inside this evaporator so as to control the pressure inside vacuum evaporator 33 such that a boiling point of NMP becomes 130° C., for example. Vacuum evaporator 33 is supplied with a necessary amount of steam for evaporating NMP. Vacuum pump 36 connected to vacuum evaporator 33 is also used for attaining a negative pressure on the permeation side of pervaporation apparatus 13. Vacuum evaporator 33 is provided to remove hard-volatile impurities such as ionic impurities and fine particles.

Piping 40 used for discharging NMP vaporized inside the vacuum evaporator is provided at an outlet of vacuum evaporator 33. Piping 40 is connected to heater 34 so as to supply the vaporized NMP at 130° C., for example, to heater 34 as a heat source. NMP vapor supplied to heater 34 is condensed during heating the liquid mixture. Hence, heater 34 heats the liquid mixture as well as functions as a condenser for NMP vapor. Without using an external heat source such as steam as a medium for heating in heater 34, it is possible to carry out direct heat-exchange between NMP vapor and the liquid mixture containing NMP and water. Accordingly, it becomes unnecessary to excessively increase the temperature of NMP vapor, so that energy efficiency becomes increased. Cooler 15 and microfiltration membrane 18 are connected in this order to an outlet on an NMP vapor side of heater 34. NMP is cooled into a complete liquid state by cooler 15, and fine particles are eventually removed by microfiltration membrane 18. As a result, purified NMP can be obtained from an outlet of microfiltration membrane 18. In this configuration, if a concentration of NMP in the liquid mixture in raw solution tank 31 is 80 mass %, that is, if water is 20 mass %, for example, water concentration in NMP obtained at the outlet of microfiltration membrane 18 can be set to be approximately 0.02 mass %.

Now, a heat recovery efficiency in heater 34 in this system will be discussed. If an organic solvent and water are separated from each other using pervaporation apparatus 13, water is brought to pass through pervaporation membrane 14, and thus, it is necessary to apply heat equivalent to evaporative latent heat of water in advance. The evaporative latent heat of water is 2.30 MJ/kg, and the evaporative latent heat of NMP is 439 kJ/kg. Therefore, even if all condensation-radiation heat of NMP is supplied, this heat amount cannot satisfy the evaporative latent heat of water in pervaporation apparatus 13. This means that all the amount of heat supplied to vacuum evaporator 33 can be recovered by heater 34. Hence, in the present embodiment, it is possible to attain the same energy saving performance as that in the case of using pervaporation apparatus 13 alone, and also to more securely remove ionic impurities, fine particles, and the like from NMP because vacuum evaporator 33 is additionally provided. With respect to heating of the liquid mixture supplied to pervaporation apparatus 13, it is preferable in light of heat efficiency and the like to arrange heater 34 that heats the liquid mixture with condensation heat of NMP vapor at a preceding position, and heater 12 that heats the liquid mixture with steam up to a desired temperature at subsequent position to heater 34, compared with the case of providing these heaters in a reverse order (i.e., the order of heater 12 and heater 34).

Figure 4:
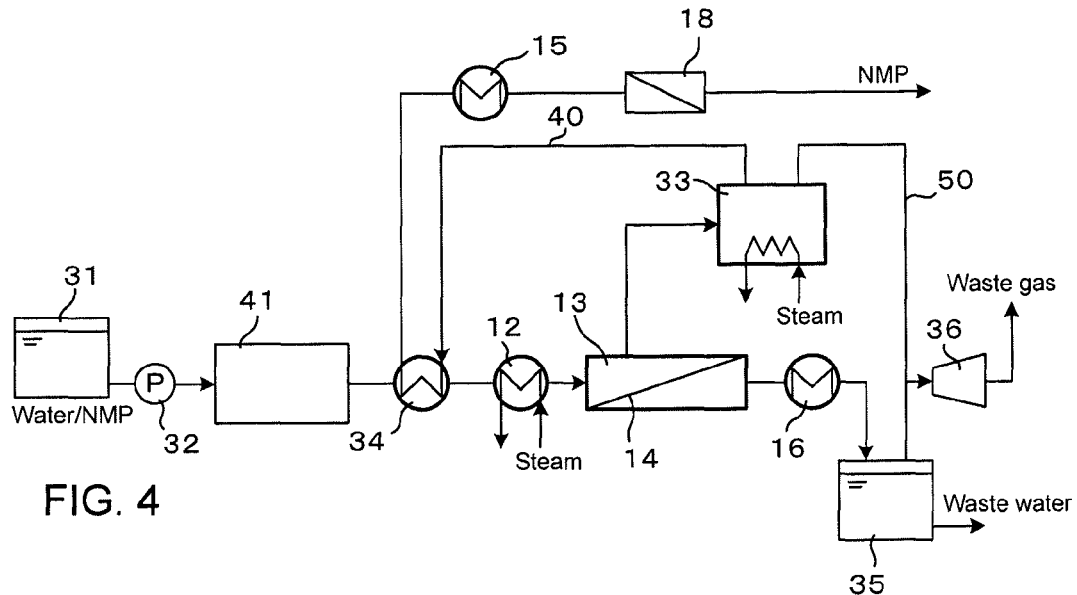
FIG. 4 is a view illustrating a configuration of an organic solvent purification system according to the embodiment equipped with an ion exchanger.

In the case in which the purified organic solvent is required to have an extremely low concentration of ionic impurities, or in the case in which a large amount of ionic impurities is contained in the liquid mixture of the organic solvent and water, removal of the ionic impurities sometimes becomes insufficient by using vacuum evaporator 33 alone. To cope with this, the organic solvent purification system shown in FIG. 3 may be additionally provided with an ion exchanger filled with an ion exchange resin. Since the ion exchange resin exhibits a higher ion removal performance under presence of water, it is more advantageous to carry out processing using the ion exchange resin prior to separation of the organic solvent from water when separating the organic solvent from the liquid mixture containing the organic solvent, water and ionic impurities, and purifying the organic solvent. FIG. 4 illustrates an organic solvent purification system including an ion exchanger. This organic solvent purification system is configured such that, in the system shown in FIG. 3, ion exchanger 41 is provided at an outlet of pump 32, the liquid mixture processed by ion exchanger 41 is heated by heater 34 and heater 12, and is then supplied to pervaporation apparatus 13. Ion exchanger 41 removes ionic impurities contained in the liquid mixture, and is configured, for example, to be filled with an anion exchange resin or with a mixed bed of an anion exchange resin and a cation exchange resin.

Figure 5:
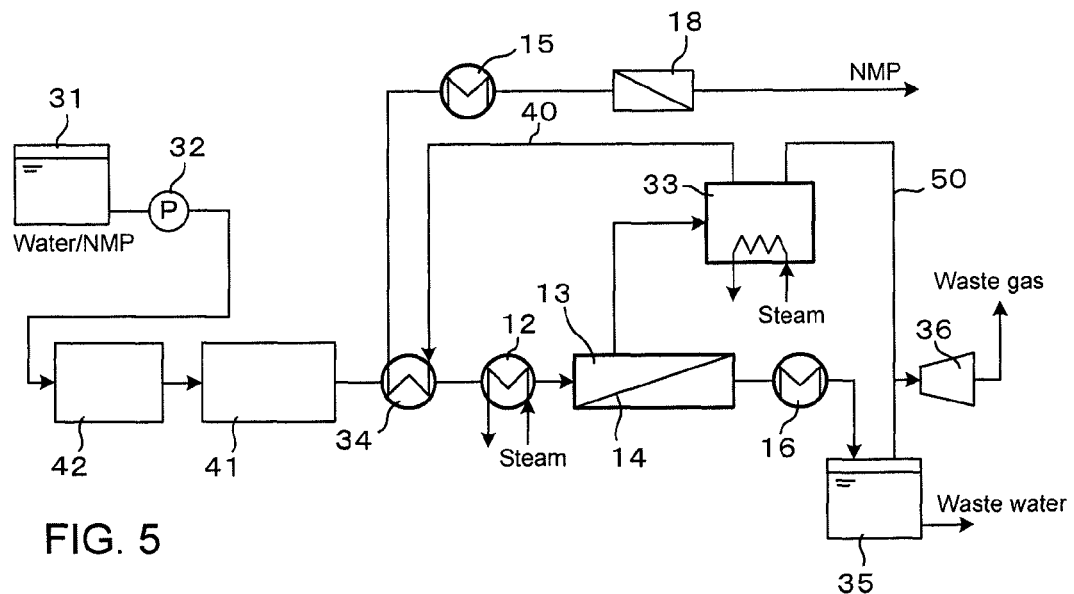
FIG. 5 is a view illustrating a configuration of the organic solvent purification system of the embodiment equipped with an ion exchanger and a degassing apparatus.

When the organic solvent is separated from water by the pervaporation method, dehydration efficiency, that is, separation efficiency between the organic solvent and water becomes enhanced by heating the supplied liquid to the pervaporation apparatus to increase temperature of the supplied liquid. However, this heating might cause oxidization, thus deteriorating the organic solvent. According to the studies by the present inventors, it has been found that as amount of dissolved oxygen in the liquid mixture containing the organic solvent and water is greater, oxidization of the organic solvent is encouraged more. To solve this, it may be considered to remove gas components in the liquid mixture of the organic solvent and water, and then supply this liquid mixture to pervaporation apparatus 13. FIG. 5 illustrates a configuration of the organic solvent purification system including a degassing apparatus to remove gas components in the liquid mixture.

The organic solvent purification system shown in FIG. 5 is configured such that, in the system shown in FIG. 4, degassing apparatus 42 to remove gas components in the liquid mixture supplied from pump 32 is provided between pump 32 and ion exchanger 41. As degassing apparatus 42, there may be used an oxygen removal apparatus to remove oxygen by adding hydrogen to be contact with a palladium catalyst, but the oxygen removal apparatus cannot remove gas components other than oxygen, such as dissolved carbon dioxide. The dissolved carbon dioxide becomes a load with respect to the ion exchange resin, in particular, to the anion exchange resin in ion exchanger 41. Therefore, it is preferable to use one configured to remove carbon dioxide in addition to oxygen as degassing apparatus 42. It might be possible to send an inert gas, such as nitrogen and argon, into the liquid to remove dissolved oxygen, but this method cannot carry out rapid degassing. In light of this, it is preferable to use one using a degassing membrane as degassing apparatus 42. By using such a degassing membrane, it is possible to rapidly remove dissolved oxygen and dissolved carbon dioxide in the liquid mixture without supplying hydrogen and an inert gas.

Examples of a membrane material and a potting material used for forming the degassing membrane may include polyolefin, polytetrafluoroethylene (PTFE), tetrafluoroethylene-perfluoroalkylvinylether copolymer (PFA), polyurethane, and epoxy resin, etc. However, since the organic solvent such as NMP has a property to dissolve some organic materials, it is preferable to form the degassing membrane by polyolefin, PTFE or PFA in the system shown in FIG. 5. With respect to a mechanical structure of the degassing membrane, there are a porous membrane formed based on assumption of usage in water, and a nonporous membrane formed based on assumption of usage in a liquid whose surface tension is smaller. In this case, the liquid mixture containing a large amount of the organic solvent such as NMP is processed, and thus it is preferable to use a nonporous membrane. An example of the degassing membrane usable in the system shown in FIG. 5 is a polyolefin membrane that is disclosed in JP 2004-105797A.

In the organic solvent purification system as illustrated in FIG. 5, the liquid mixture from which the dissolve oxygen and the dissolved carbon dioxide are removed by degassing apparatus 42 is supplied to ion exchanger 41. Thereafter, the liquid mixture after being heated by heaters 34, 12 up to appropriately 120° C., for example, is supplied to pervaporation apparatus 13. Since the carbon dioxide concentration in the liquid mixture is reduced, the load to ion exchanger 41 is reduced. Consequently, it is possible to prolong a replacement period of the ion exchange resin in ion exchanger 41. The dissolved oxygen is reduced, thus suppressing oxidization and deterioration of NMP. The system shown in FIG. 5 is provided with ion exchanger 41, but an organic solvent purification system including no ion exchanger may also be provided with degassing apparatus 42.

Figure 6:
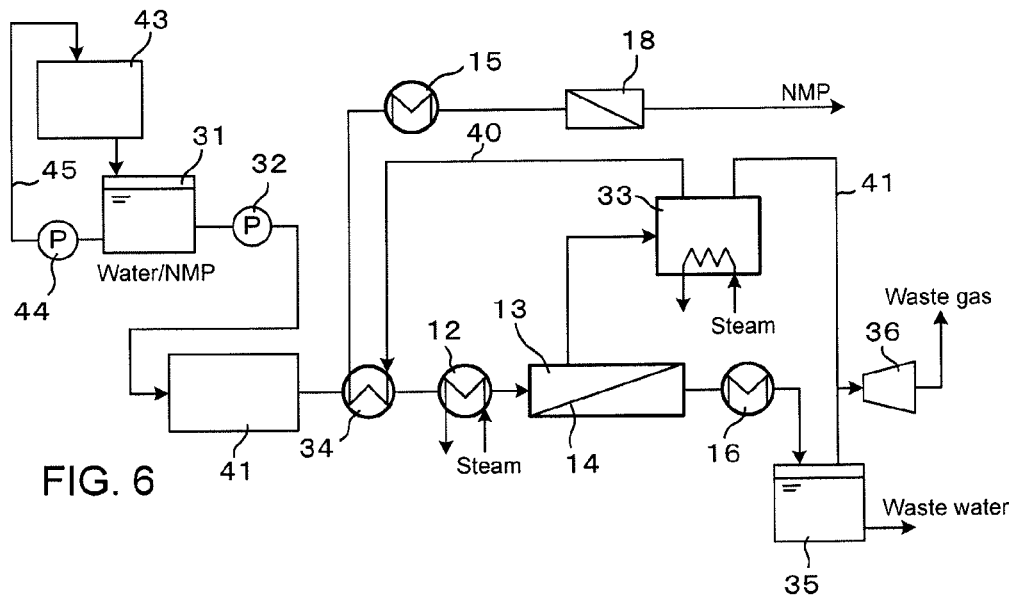
FIG. 6 is a view illustrating another example of the configuration of the organic solvent purification system according to the embodiment equipped with an ion exchanger and a membrane degassing apparatus.

FIG. 6 illustrates another example of the organic solvent purification system including the degassing apparatus. The organic solvent purification system shown in FIG. 6 is configured such that, in the organic solvent purification system shown in FIG. 5, membrane degassing apparatus 43 having a degassing membrane is used as the degassing apparatus, and pump 44 is additionally provided to the system. In the system shown in FIG. 6, membrane degassing apparatus 43 is not disposed immediately before ion exchanger 41, but is so disposed as to degas the liquid mixture in raw solution tank 31, instead. There is provided piping 45 that connects a bottom part and an upper part of raw solution tank 31 to circulate the liquid mixture therethrough by pump 44. Membrane degassing apparatus 43 is disposed on this piping 45. The degassed liquid mixture in raw solution tank 31 is supplied to ion exchanger 41 by pump 32.

In general, an optimum liquid flow rate for the membrane degasification does not always coincide with an optimum liquid flow rate for the operation of the pervaporation apparatus. In the configuration shown in FIG. 6, by independently controlling two pumps 32, 44, it is possible to independently set the flow rate of the liquid mixture in membrane degassing apparatus 43 and the flow rate of the liquid mixture supplied to pervaporation apparatus 13, thereby respectively carrying out the membrane degasification and the pervaporation under optimum conditions. Only the membrane degasification is continuously carried out by using pump 44 having a smaller capacity even in a period in which no NMP purification is carried out, thereby attaining a rapid start-up of the process at the start time of the purification of NMP. Although the system shown in FIG. 6 is provided with ion exchanger 41, an organic solvent purification system including no ion exchanger may also be provided with membrane degassing apparatus 43.

Figure 7:
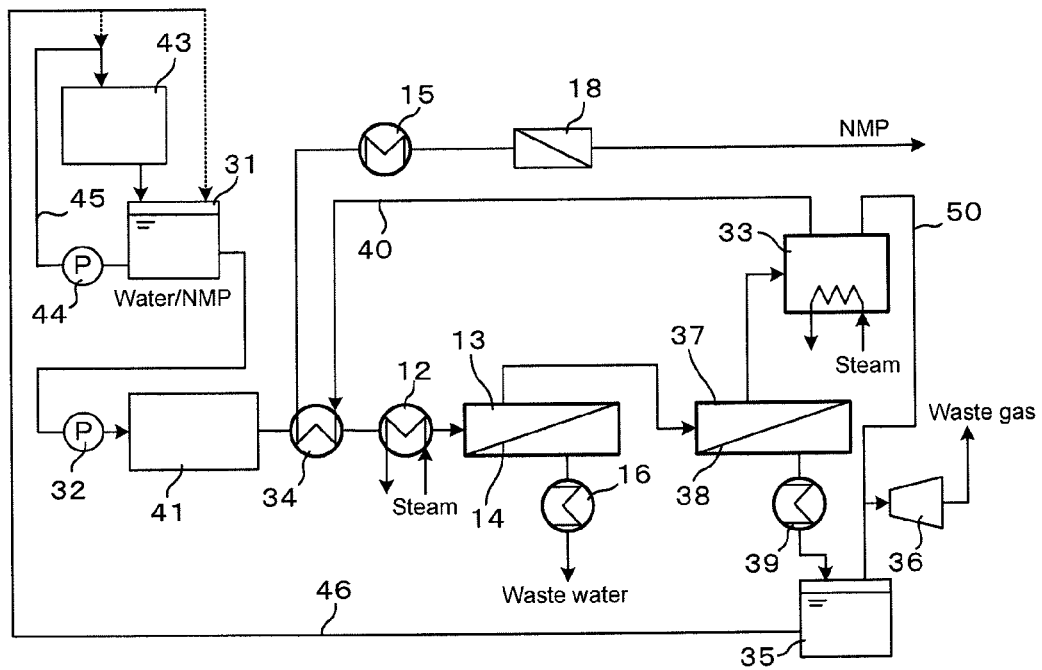
FIG. 7 is a view illustrating a configuration of an organic solvent purification system according to further another embodiment of the present invention.

FIG. 7 illustrates a configuration of the organic solvent purification system of further another embodiment of the present invention. In each system shown in FIGS. 3 to 6, single-stage pervaporation apparatus 13 is used, and in this case, the water component might remain in the obtained organic solvent such as NMP, or NMP might remain in the water to be discharged via condenser 16 as waste water. In the organic solvent purification system shown in FIG. 7, two pervaporation apparatuses 13, 37 are connected in series to carry out the pervaporation processing in two stages.

Specifically, the organic solvent purification system shown in FIG. 7 is configured such that, in the system shown in FIG. 6, the liquid discharged from the concentration side of pervaporation apparatus 13 is supplied to second-stage pervaporation apparatus 37. Focusing on the flow of NMP, these pervaporation apparatuses 13, 37 are connected in series. Second-stage pervaporation apparatus 37 is also provided with pervaporation membrane 38 formed of zeolite, for example. NMP is separated from the concentration side of second-stage pervaporation apparatus 37, and the separated NMP is supplied to vacuum evaporator 33, as similar to the apparatus shown in FIG. 6. The vapor of NMP from vacuum evaporator 33 is sent via piping 40 to heater 34 so as to be used for heating the liquid mixture, and then NMP is sent through cooler 15 and microfiltration membrane 18 to be produced into purified NMP. The water component appearing on the permeation side of first-stage pervaporation apparatus 13 is cooled and condensed by condenser 16, and is reserved in a condensed water tank (not shown), and is then discharged, as similar to each system shown in FIGS. 3 to 6.

The water component obtained from the permeation side of second-stage pervaporation apparatus 37 is cooled to be condensed by condenser 39, and is then reserved in permeation water tank 35. In order to secure a negative pressure on the permeation side of second-stage pervaporation apparatus 37, vacuum pump 36 is also connected to permeation water tank 35. The water containing NMP that is reserved in permeation water tank 35 is returned to a preceding position of first-stage pervaporation apparatus 13 via piping 46. In the shown system, water reserved in permeation water tank 35 is returned to an inlet of membrane degassing apparatus 43 or to raw solution tank 31. However, the return destination of water reserved in permeation water tank 35 is not limited to the inlet of membrane degassing apparatus 43 or to raw solution tank 31, but water reserved in permeation water tank 35 may be returned to the inlet of heater 34 or of heater 12, for example.

Pervaporation membranes 14, 38 used in pervaporation apparatuses 13, 37 will be described. Dehydration performance of pervaporation apparatuses 13, 37 depends on the difference in water component density between both sides of each pervaporation membrane 14, 38, that is, the difference in water component density between a space on the concentration side and a space on the permeation side, and also depends on the degree of vacuum on the permeation side. Specifically, as the water component density in the space on the concentration side is greater, or the degree of vacuum on the permeation side is greater, that is, an absolute pressure is smaller, the dehydration performance becomes enhanced more. For example, if water concentration in the liquid mixture is 20 mass %, first-stage pervaporation apparatus 13 can separate a large amount of water due to a great difference in water component density. To the contrary, second-stage pervaporation apparatus 37 can separate only a small amount of water because second-stage pervaporation apparatus 37 processes the liquid mixture that has already been dehydrated. Meanwhile, a permeation amount of NMP through the pervaporation membrane does not greatly depend on the difference in water component density. Hence, the NMP concentration in the water vapor appearing on the permeation side of first-stage pervaporation apparatus 13 is extremely small, and the NMP concentration in the water vapor appearing on the permeation side of second-stage pervaporation apparatus 37 is greater than the former NMP concentration. In the present embodiment, the water component that appears on the permeation side of second-stage pervaporation apparatus 37 and contains more NMP is returned to the preceding position of first-stage pervaporation apparatus 13, thereby further increasing a recovering rate of NMP, and thus suppressing emission of NMP in the environment. The amount of water component passing through second-stage pervaporation apparatus 37 is smaller than that in first-stage pervaporation apparatus 13, and decrease in dehydration efficiency due to the return of this water component to the preceding position of first-stage pervaporation apparatus 13 is restrictive.

A zeolite membrane is preferably utilized for each pervaporation membrane 14, 38. There are plural types of zeolite, such as A-type, Y-type, T-type, MOR-type and CHA-type, depending on the skeletal structure thereof and the ratio between silicon and aluminum contained therein. As the ratio of silicon relative to aluminum is greater, zeolite becomes more hydrophobic. Among these types of zeolite, the A-type zeolite is particularly excellent in dehydration efficiency, so that the A-type zeolite can be used as each pervaporation membrane 14, 38 of each pervaporation apparatus 13, 37 in the present embodiment. As pervaporation membrane 14 of first-stage pervaporation apparatus 13, it may be preferable in some cases to use the T-type, the Y-type or the CHA-type zeolite membrane other than the A-type zeolite, for example. The A-type zeolite is likely to cause leakage or deterioration of performance when the water component concentration is high or when impurities such as acid are contained in the liquid mixture. To the contrary, the performance of the other types of zeolite than the A-type zeolite can be maintained in a longer term under the environments described above. As aforementioned, pervaporation membrane 14 of first-stage pervaporation apparatus 13 is not required to have a dehydration performance as high as that of pervaporation membrane 38 of second-stage pervaporation apparatus 37. Since the water vapor from the permeation side of first-stage pervaporation apparatus 13 is emitted to the outside of the system, requirement for preventing leakage of pervaporation membrane 14 is particularly high. Hence, as pervaporation membrane 14 of first-stage pervaporation apparatus 13, there may be used a pervaporation membrane including the A-type zeolite and at least one type of zeolite selected from the other types (e.g., the T-type, the Y-type, the MOR-type and the CHA-type) of zeolite as aforementioned. In any of these cases, it is preferable to configure pervaporation membrane 38 of second-stage pervaporation apparatus 37 by the A-type zeolite. Since the liquid at the inlet of second-stage pervaporation apparatus 37 has been greatly dehydrated already, and has a small water content, the water component of this liquid at the inlet is very unlikely to cause bad influences on the membrane performance. Because of the less water content in the liquid at the inlet, a driving force of the dehydration becomes smaller, so that each membrane other than A-type is required to have a greater membrane area than that of the A-type membrane. Consequently, in case of using the membranes of the other types than the A-type membrane, apparatus scale and cost for apparatus is likely to become larger.

The dehydration performance of the pervaporation apparatus has positive correlation with a membrane area of the pervaporation membrane per unit flow-rate of the supplied liquid mixture, that is, a value obtained by dividing a membrane area of the pervaporation membrane by the flow rate of the liquid mixture. Hence, in order to obtain a dehydration performance necessary for a single pervaporation apparatus, it is required to increase the membrane area of the pervaporation membrane. In the meantime, the permeation amount of NMP has positive correlation with the membrane area of the pervaporation membrane. Thus, if a single pervaporation apparatus having a greater membrane area is used in order to enhance the dehydration performance, the permeation amount of NMP becomes increased in accordance with this increase in membrane area. To the contrary, in the present embodiment, first-stage pervaporation apparatus 13 is only required to dehydrate part of a necessary dehydration amount, and there is no necessity to excessively increase the membrane area thereof. In second-stage pervaporation apparatus 37, since NMP having passed therethrough is returned to raw solution tank 31 side, there occurs no problem even if the membrane area is increased in order to enhance the dehydration performance. In other words, a balance between the dehydration amount and the permeation amount of NMP is considered in first-stage pervaporation apparatus 13, but it is unnecessary to consider such a balance in second-stage pervaporation apparatus 37. In this manner, two pervaporation apparatuses 13, 37 are arranged in series, and NMP passing through second-stage pervaporation apparatus 37 is collected, thereby obtaining a necessary dehydration performance as well as suppressing emission amount of NMP to the outside of the system.

REFERENCE SIGNS LIST 12, 34 heater
13, 37 pervaporation apparatus
14, 38 pervaporation membrane
15 cooler
16, 39 condenser
18 microfiltration membrane
31 raw solution tank
33 vacuum evaporator
35 permeation water tank
36 vacuum pump
41 ion exchanger
42 degassing apparatus
43 membrane degassing apparatus

The invention claimed is:

1. An organic solvent purification system that separates an organic solvent having a boiling point of more than 100° C. at 1 atm from a liquid mixture containing water and the organic solvent, and purifies the organic solvent, the organic solvent purification system comprising:
    a heater that heats the liquid mixture;
    a pervaporation apparatus provided at subsequent position of said heater, the pervaporation apparatus including a pervaporation membrane and separating the organic solvent from the water;
    a vacuum evaporator to which the organic solvent collected from a concentration side of said pervaporation apparatus is supplied; and
    piping that supplies said heater with the organic solvent vaporized in said vacuum evaporator as a heat source of said heater.

2. The organic solvent purification system according to claim 1, further comprising an ion exchanger provided at preceding position of said heater, the ion exchanger carrying out ion exchange processing of the liquid mixture.

3. The organic solvent purification system according to claim 1, comprising a degassing apparatus provided at preceding position of said heater, the degassing apparatus removing gas components contained in the liquid mixture.

4. The organic solvent purification system according to claim 1, further comprising:
    a degassing apparatus that is supplied with the liquid mixture, and removes gas components contained in the liquid mixture; and
    an ion exchanger that carries out ion exchange processing of the liquid mixture processed by said degassing apparatus,
    wherein the liquid mixture after being subjected to the ion exchange processing is supplied to said heater.

5. The organic solvent purification system according to claim 3, wherein said degassing apparatus includes a degassing membrane.

6. The organic solvent purification system according to claim 3, further comprising:
    a tank that reserves the liquid mixture; and
    piping that circulates the liquid mixture between said degassing apparatus and said tank.

7. The organic solvent purification system according to claim 1, wherein
    said pervaporation apparatus is configured by connecting in series a first pervaporation apparatus and a second pervaporation apparatus to which a liquid discharged from a concentration side of said first pervaporation apparatus is supplied,
    the organic solvent collected from a concentration side of said second pervaporation apparatus is supplied to said vacuum evaporator, and
    said organic solvent purification system further includes piping that circulates a liquid discharged from a permeation side of said second pervaporation apparatus to preceding position of said first pervaporation apparatus.

8. The organic solvent purification system according to claim 1, wherein the organic solvent comprises N-methyl-2-pyrrolidone.

9. A method that separates an organic solvent having a boiling point of more than 100° C. at 1 atm from a liquid mixture containing water and the organic solvent, and purifies the organic solvent, the method comprising the steps of:
    heating the liquid mixture;
    separating the heated liquid mixture into the organic solvent and the water using a pervaporation membrane; and
    carrying out vacuum evaporation of the organic solvent collected from a concentration side of said pervaporation membrane,
    wherein the organic solvent vaporized through the vacuum evaporation is used as a heat source in said heating step.

10. The organic solvent purification system according to claim 2, comprising a degassing apparatus provided at preceding position of said heater, the degassing apparatus removing gas components contained in the liquid mixture.

11. The organic solvent purification system according to claim 4, wherein said degassing apparatus includes a degassing membrane.

12. The organic solvent purification system according to claim 4, further comprising:
    a tank that reserves the liquid mixture; and
    piping that circulates the liquid mixture between said degassing apparatus and said tank.

13. The organic solvent purification system according to claim 12, wherein said degassing apparatus includes a degassing membrane.

14. The organic solvent purification system according to claim 7, further comprising:
    a degassing apparatus that is supplied with the liquid mixture, and removes gas components contained in the liquid mixture; and
    an ion exchanger that carries out ion exchange processing of the liquid mixture processed by said degassing apparatus,
    wherein the liquid mixture after being subjected to the ion exchange processing is supplied to said heater.

15. The organic solvent purification system according to claim 14, wherein said degassing apparatus includes a degassing membrane.

16. The organic solvent purification system according to claim 15, further comprising:
    a tank that reserves the liquid mixture; and
    piping that circulates the liquid mixture between said degassing apparatus and said tank.

17. The organic solvent purification system according to claim 7, wherein the organic solvent comprises N-methyl-2-pyrrolidone.

18. The organic solvent purification system according to claim 14, wherein the organic solvent comprises N-methyl-2-pyrrolidone.

* * * * *